US012256895B2

(12) United States Patent
Aneja et al.

(10) Patent No.: US 12,256,895 B2
(45) Date of Patent: Mar. 25, 2025

(54) ATTACHMENTS FOR ENDOSCOPES

(71) Applicant: BOSTON SCIENTIFIC MEDICAL DEVICE LIMITED, Galway (IE)

(72) Inventors: Harchetan Singh Aneja, Amritsar (IN); Boopathi Rajarathnam, Salem (IN); Swami Upadhyay, Raipur (IN); Shalin Singh Rawat, Rishikesh (IN); Venkatesh Neelamegam, Tirupur (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 556 days.

(21) Appl. No.: 16/671,879

(22) Filed: Nov. 1, 2019

(65) Prior Publication Data
US 2020/0138274 A1    May 7, 2020

Related U.S. Application Data

(60) Provisional application No. 62/834,201, filed on Apr. 15, 2019, provisional application No. 62/834,192, (Continued)

(51) Int. Cl.
A61B 1/00      (2006.01)
A61B 1/015     (2006.01)
(Continued)

(52) U.S. Cl.
CPC ...... *A61B 1/00137* (2013.01); *A61B 1/00064* (2013.01); *A61B 1/0011* (2013.01);
(Continued)

(58) Field of Classification Search
CPC .......................... A61B 1/00137; A61B 1/0014
See application file for complete search history.

(56) References Cited

U.S. PATENT DOCUMENTS 4,198,959 A    4/1980  Otani
5,104,379 A    4/1992  Nakamura et al.
(Continued)

FOREIGN PATENT DOCUMENTS

AU    1999027921 A1    2/2000
AU    2001056987 A1    2/2000
(Continued)

OTHER PUBLICATIONS

Cook Medical—"Fusion® Wire Guide Locking Device" URL: https://www.cookmedical.com/products/esc_fswl_webds/ © Cook 2021.
(Continued)

*Primary Examiner* — Timothy J Neal
(74) *Attorney, Agent, or Firm* — Seager, Tufte & Wickhem, LLP

(57) ABSTRACT

Attachments for endoscopes as well as methods for making and using attachments are disclosed. An example attachment may include a housing. One or more angled locking members may extend from an inner surface of the housing. The angled locking members may be designed to engage a biopsy port of an endoscope. One or more stabilizing members may extend from the inner surface of the housing. A locking apparatus may be coupled to the housing. A sealing member may be disposed within the housing.

20 Claims, 11 Drawing Sheets

Related U.S. Application Data filed on Apr. 15, 2019, provisional application No. 62/768,808, filed on Nov. 16, 2018, provisional application No. 62/755,024, filed on Nov. 2, 2018.

(51) Int. Cl.
*A61B 1/018* (2006.01)
*A61B 10/02* (2006.01)
*A61B 10/04* (2006.01)
*B29D 99/00* (2010.01)

(52) U.S. Cl.
CPC ........ *A61B 1/0014* (2013.01); *A61B 1/00147* (2013.01); *A61B 1/015* (2013.01); *A61B 1/018* (2013.01); *A61B 10/0275* (2013.01); *A61B 10/04* (2013.01); *B29D 99/0053* (2013.01)

(56) References Cited

U.S. PATENT DOCUMENTS

| | | | |
|---|---|---|---|
| 5,312,363 A | 5/1994 | Ryan et al. | |
| 5,743,884 A | 4/1998 | Hasson et al. | |
| 5,993,379 A * | 11/1999 | Ouchi | A61B 46/10 |
| | | | 600/154 |
| 6,200,262 B1 | 3/2001 | Ouchi | |
| 6,605,075 B1 | 8/2003 | Burdulis | |
| 7,060,052 B2 | 6/2006 | Windheuser et al. | |
| 7,226,411 B2 | 6/2007 | Akiba | |
| 7,473,221 B2 | 1/2009 | Ewers et al. | |
| 7,637,863 B2 | 12/2009 | Deal et al. | |
| 7,670,285 B2 | 3/2010 | Yamaya | |
| 7,670,316 B2 | 3/2010 | Windheuser et al. | |
| 7,803,107 B2 | 9/2010 | Carrillo | |
| 7,967,744 B2 | 6/2011 | Kaye et al. | |
| 8,012,129 B2 | 9/2011 | Bettuchi et al. | |
| 8,152,774 B2 | 4/2012 | Pasqualucci | |
| 8,231,525 B2 | 7/2012 | Cohen et al. | |
| 8,333,693 B2 | 12/2012 | Hamazaki | |
| 8,343,041 B2 | 1/2013 | Byers et al. | |
| 8,480,570 B2 | 7/2013 | Tinkham et al. | |
| 8,647,256 B2 | 2/2014 | Carrillo, Jr. | |
| 8,702,596 B2 | 4/2014 | Kaye et al. | |
| 8,753,264 B2 | 6/2014 | Carrillo, Jr. et al. | |
| 8,974,377 B2 | 3/2015 | Yamane | |
| 9,089,261 B2 | 7/2015 | Greenburg et al. | |
| 9,101,738 B2 | 8/2015 | Eden | |
| 9,131,831 B2 | 9/2015 | Byers et al. | |
| 9,149,173 B2 | 10/2015 | Scopton et al. | |
| 9,566,145 B2 | 2/2017 | Trainor et al. | |
| 9,622,776 B2 | 4/2017 | Oberlaender et al. | |
| 9,955,998 B2 | 5/2018 | Kleyman | |
| 9,986,895 B2 | 6/2018 | Meloul | |
| 2005/0171402 A1 | 8/2005 | Cohen et al. | |
| 2006/0195117 A1 | 8/2006 | Rucker et al. | |
| 2007/0238928 A1 | 10/2007 | Maseda et al. | |
| 2007/0244356 A1 | 10/2007 | Carrillo et al. | |
| 2007/0282166 A1 | 12/2007 | Ayala et al. | |
| 2007/0293719 A1 | 12/2007 | Scopton et al. | |
| 2009/0005799 A1 | 1/2009 | Franer et al. | |
| 2009/0088600 A1 | 4/2009 | Meloul | |
| 2009/0287052 A1 | 11/2009 | Amos et al. | |
| 2009/0287111 A1* | 11/2009 | Kaye | A61B 1/00137 |
| | | | 600/101 |
| 2010/0081878 A1 | 4/2010 | Byers et al. | |
| 2010/0087705 A1 | 4/2010 | Byers et al. | |
| 2010/0240956 A1 | 9/2010 | Secrest et al. | |
| 2012/0004507 A1 | 1/2012 | Kaye | |
| 2012/0071713 A1 | 3/2012 | Kaye et al. | |
| 2012/0253128 A1* | 10/2012 | Yamane | A61B 1/00062 |
| | | | 600/154 |
| 2013/0085335 A1* | 4/2013 | Yamane | A61B 1/00137 |
| | | | 600/123 |
| 2013/0150793 A1 | 6/2013 | Beissel et al. | |
| 2013/0304116 A1 | 11/2013 | Yamane | |
| 2015/0190170 A1 | 7/2015 | Frederick et al. | |
| 2016/0206859 A1 | 7/2016 | Eden | |
| 2017/0202438 A1 | 7/2017 | Ogi | |
| 2017/0319828 A1 | 11/2017 | Doepker et al. | |
| 2018/0014717 A1* | 1/2018 | Benn | A61B 1/00121 |
| 2018/0310806 A1 | 11/2018 | Gavalis et al. | |
| 2019/0046016 A1 | 2/2019 | Rajarathnam et al. | |
| 2020/0138272 A1 | 5/2020 | Neelamegam et al. | |
| 2020/0138273 A1 | 5/2020 | Neelamegam et al. | |
| 2020/0138276 A1 | 5/2020 | Aneja et al. | |
| 2020/0138277 A1 | 5/2020 | Neelamegam et al. | |
| 2020/0138419 A1 | 5/2020 | Aneja et al. | |

FOREIGN PATENT DOCUMENTS

| | | |
|---|---|---|
| CN | 105816208 A | 8/2016 |
| CN | 205697867 U | 11/2016 |
| EP | 1997444 A2 | 12/2008 |
| EP | 1406691 B1 | 1/2010 |
| EP | 2505119 A1 | 10/2012 |
| EP | 2323540 B1 | 11/2012 |
| EP | 2564758 A1 | 3/2013 |
| EP | 2574271 A1 | 4/2013 |
| EP | 2564758 B1 | 6/2014 |
| EP | 2574271 B1 | 11/2014 |
| EP | 2020901 B1 | 7/2016 |
| JP | S6129703 U | 2/1986 |
| JP | 2001104315 A | 4/2001 |
| JP | 2005080867 A | 3/2005 |
| JP | 2008123063 A | 5/2008 |
| JP | 2009268777 A | 11/2009 |
| WO | 2005011791 A2 | 2/2005 |
| WO | 2005011791 A3 | 8/2005 |
| WO | 2007117750 A2 | 10/2007 |
| WO | 2008101286 A1 | 8/2008 |
| WO | 2009143129 A1 | 11/2009 |
| WO | 2009143137 A1 | 11/2009 |
| WO | 2018024109 A1 | 2/2018 |

OTHER PUBLICATIONS

International Search Report and Written Opinion for application No. PCT/IB2019/059411, dated Jun. 25, 2020, 14 pages.
International Search Report and Written Opinion for International application No. PCT/IB2019/059409, mailed on Feb. 13, 2020, 11 pages.
International Search Report and Written Opinion for International application No. PCT/IB2019/059408, mailed on Feb. 14, 2020, 12 pages.
International Search Report and Written Opinion for International application No. PCT/IB2019/059407, mailed on Feb. 14, 2020, 11 pages.
International Search Report and Written Opinion for International application No. PCT/IB2019/059413, mailed on Feb. 17, 2020, 10 pages.
International Search Report and Written Opinion for International application No. PCT/IB2019/059404, mailed on Feb. 17, 2020, 10 pages.

* cited by examiner

ATTACHMENTS FOR ENDOSCOPES

PRIORITY

This application claims the benefit of priority under 35 USC § 119 to U.S. Provisional Patent Application Ser. No. 62/755,024, filed Nov. 2, 2018 and titled "Attachments for Endoscopes," U.S. Provisional Patent Application Ser. No. 62/768,808, filed Nov. 16, 2018 and titled "Internal Seal for Biopsy Cap," U.S. Provisional Patent Application Ser. No. 62/834,192, filed Apr. 15, 2019 and titled "Biopsy Cap and Biopsy Cap Housing," and to U.S. Provisional Patent Application Ser. No. 62/834,201, filed Apr. 15, 2019 and titled "Devices, Systems, and Methods For Providing Sealable Access To A Working Channel," the disclosures of which are incorporated by reference herein in their entirety and for all purposes.

TECHNICAL FIELD

The present disclosure relates generally to the field of medical instruments. More particularly, the present disclosure pertains to medical instruments for use with an endoscope, such as a biopsy cap and a biopsy cap housing with improved stability and stress distribution, for example, to securely attach to an endoscope biopsy port.

BACKGROUND

Conventional endoscope biopsy cap housings and biopsy caps can include a variety of deficiencies which may contribute—both individually and cumulatively—to component breakage, unnecessarily complicated or additional procedural steps and/or prolonged procedure times. For example, conventional biopsy cap housings tend to permit axial and rotational movement of the housing and/or cap during device exchange. In addition, exchange of larger diameter medical instruments (e.g., catheters, stent introducers, etc.) through the biopsy cap tends to exert a radially outward force which may cause the two center-split halves of conventional biopsy cap housings to partially or completely separate/disengage from each other. Adhesives applied to the center-split halves may minimize such separation but result in increased assembly time and cost. Locking or unlocking a guidewire to the hook(s) located on one side of a conventional biopsy cap housing tends to exert a radially outward force on one of the center-split halves, which may cause the center-split halves to move in opposite directions and partially or completely separate/disengage from each other. Excessive flexing due to lateral forces applied to one or both center-split halves, e.g., during disengagement of the biopsy cap housing from the biopsy port, may concentrate stress on the locks which secure the biopsy cap housing to the endoscope port, resulting in a fracture of one or more of the locks. Any fracturing of components or separation between the center-split halves resulting from these forces may result in compromised stability between the biopsy cap housing and the endoscope biopsy port. In addition, the cumulative effects of these separation forces may decrease the operational longevity of the biopsy cap housing.

A variety of advantageous medical outcomes may therefore be realized by the biopsy cap and biopsy cap housing embodiments of the present disclosure.

BRIEF SUMMARY

This disclosure provides design, material, manufacturing method, and use alternatives for medical instruments. An attachment for an endoscope is disclosed. The attachment comprises: a housing; one or more angled locking members extending from an inner surface of the housing, the angled locking members being designed to engage a biopsy port of an endoscope; one or more stabilizing members extending from the inner surface of the housing; a locking apparatus coupled to the housing; and a sealing member disposed within the housing.

Alternatively or additionally to any of the embodiments above, the one or more angled locking members include a first angled locking member disposed on a first side of the inner surface of the housing and a second angled locking member disposed on a second side of the inner surface of the housing.

Alternatively or additionally to any of the embodiments above, the one or more angled locking members include a first angled locking member and wherein the first angled locking member includes a bent region.

Alternatively or additionally to any of the embodiments above, the one or more angled locking members include a first angled locking member and wherein the first angled locking member is substantially V-shaped.

Alternatively or additionally to any of the embodiments above, the one or more angled locking members include a first angled locking member and wherein the first angled locking member is substantially rigid.

Alternatively or additionally to any of the embodiments above, the one or more angled locking members include a first angled locking member and wherein the first angled locking member is resiliently deflectable.

Alternatively or additionally to any of the embodiments above, the one or more stabilizing members include a first stabilizing member disposed on a first side of the inner surface of the housing and a second stabilizing member disposed on a second side of the inner surface of the housing.

Alternatively or additionally to any of the embodiments above, the one or more stabilizing members include a first stabilizing member and wherein the first stabilizing member extends radially inward from the inner surface of the housing.

Alternatively or additionally to any of the embodiments above, the housing includes a skirt region.

Alternatively or additionally to any of the embodiments above, the locking apparatus includes one or more guidewire locks.

Alternatively or additionally to any of the embodiments above, the sealing member includes a biopsy cap including a resilient seal.

An attachment for an endoscope is disclosed. The attachment comprises: a housing designed to engage a biopsy port of an endoscope; a skirt region defined along a first end region of the housing; a locking region defined along a second end region of the housing; an angled locking member extending from an inner surface of the housing; a stabilizing member extending from the inner surface of the housing and disposed adjacent to the angled locking member; and a sealing member disposed within the housing.

Alternatively or additionally to any of the embodiments above, further comprising a second angled locking member extending from the inner surface of the housing and disposed opposite the angled locking member.

Alternatively or additionally to any of the embodiments above, the angled locking member includes a bent region.

Alternatively or additionally to any of the embodiments above, the angled locking member is substantially V-shaped.

Alternatively or additionally to any of the embodiments above, the angled locking member is substantially rigid.

Alternatively or additionally to any of the embodiments above, the angled locking member is resiliently deflectable.

Alternatively or additionally to any of the embodiments above, further comprising a second stabilizing member extending from the inner surface of the housing and disposed opposite the stabilizing member.

Alternatively or additionally to any of the embodiments above, the stabilizing member extends radially inward from the inner surface of the housing.

An attachment for an endoscope is disclosed. The attachment comprises: a housing designed to engage a biopsy port of an endoscope; an asymmetrical skirt region defined along a first end region of the housing; a guidewire locking region defined along a second end region of the housing; a pair of angled locking members extending from an inner surface of the housing; a pair of stabilizing members extending from the inner surface of the housing and disposed adjacent to the pair of angled locking members; and a biopsy cap disposed within the housing, the biopsy cap including a resilient seal member.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
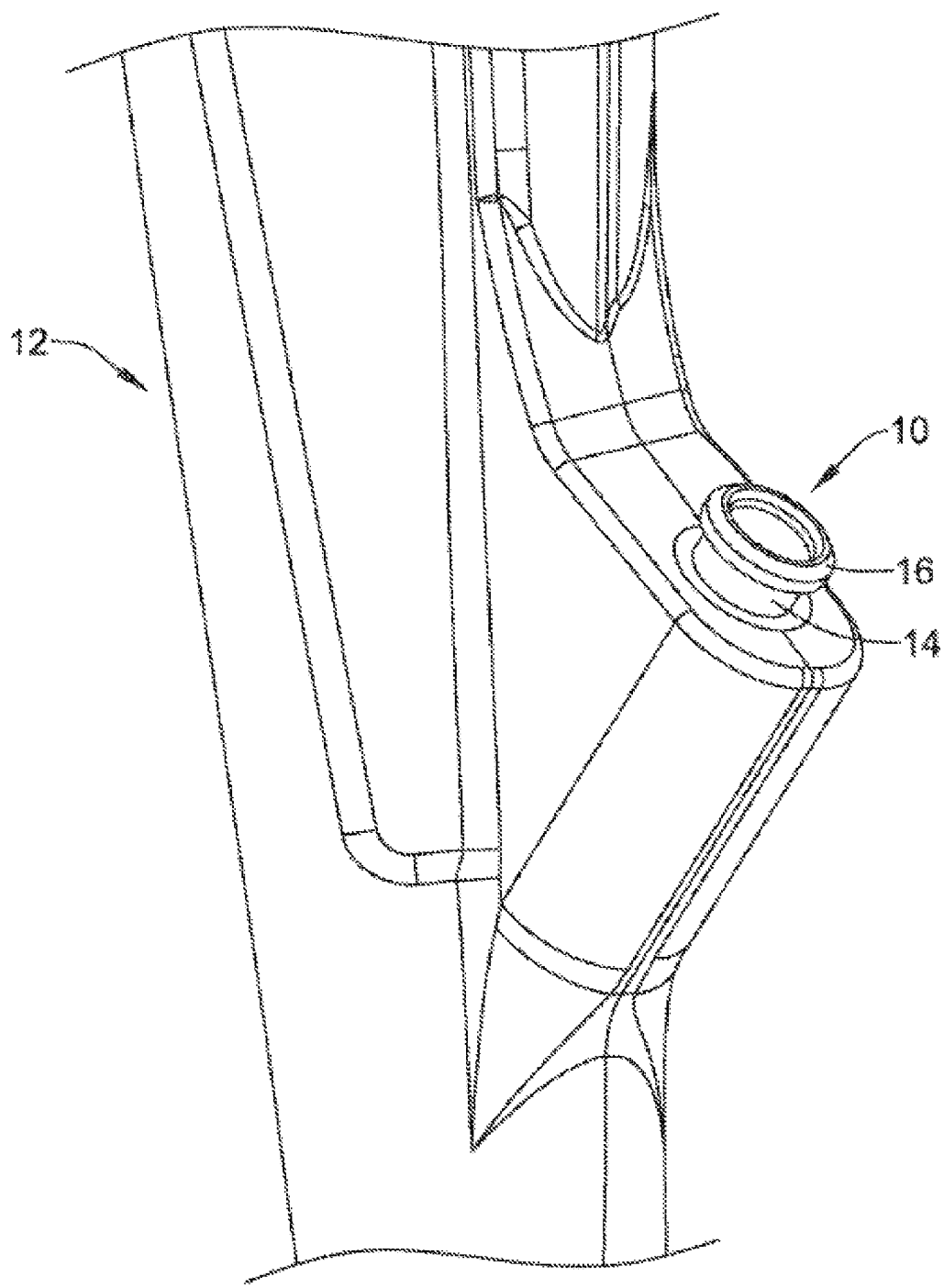
FIG. 1 is a plan view of a portion of an including a biopsy port to a working channel of the endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

In various embodiments, features and advantages of providing sealable access to a working channel, e.g., of an endoscope, may be realized in combination with a biopsy cap and biopsy cap housing. Such sealable access to a working channel, which may be reinforced, may be implemented with features throughout the disclosures of U.S. patent application Ser. No. 16/100,960, filed Aug. 10, 2018 and titled "Biopsy Cap For Use With Endoscope," United States patent application, filed on even date herewith and titled "Devices, Systems, And Methods For A Biopsy Cap And Housing," United States patent application, filed on even date herewith and titled "Biopsy Cap And Biopsy Cap Housing," United States patent application filed on even date herewith and titled, "Devices, Systems, And Methods For Providing Sealable Access To A Working Channel," United States patent application, filed on even date herewith and titled "Internal Seal for Biopsy Cap," United States patent application, filed on even date herewith and titled "Devices, Systems, and Methods for Providing Sealable Access to a Working Channel," which are each incorporated by reference in their entirety and for all purposes.

During endoscopic procedures, a medical instrument such as a guidewire, catheter, endoscopic instrument, or the like may be inserted through a working channel of the endoscope. A port (e.g., a "biopsy port") along the endoscope may provide access to the working channel. During use, it may be desirable to couple a biopsy cap to the biopsy port. The biopsy cap may have one more seals or sealing members. The seals may be designed to seal against the biopsy port and/or against instrument(s) that may be extended through the biopsy cap into the working channel. During some interventions, it may be desirable to secure the position of a medical instrument (e.g., a guidewire) relative to the endoscope. In order to secure the medical instrument, a locking mechanism may be secured to the endoscope and/or the biopsy cap. Disclosed herein are endoscope attachments or biopsy cap assemblies that may include a number of features including a biopsy cap housing, biopsy cap, a locking mechanism, as well as other features.

FIG. 1 illustrates a portion of a biopsy port 10 of an example endoscope 12. The biopsy port 10 may include a stem or neck region 14 and an end or flanged region 16. The biopsy port 10 serves as an access point to a channel (e.g., a working channel) of the endoscope 12. The biopsy port 10, in general, may be designed to receive a biopsy cap.

Figure 2:
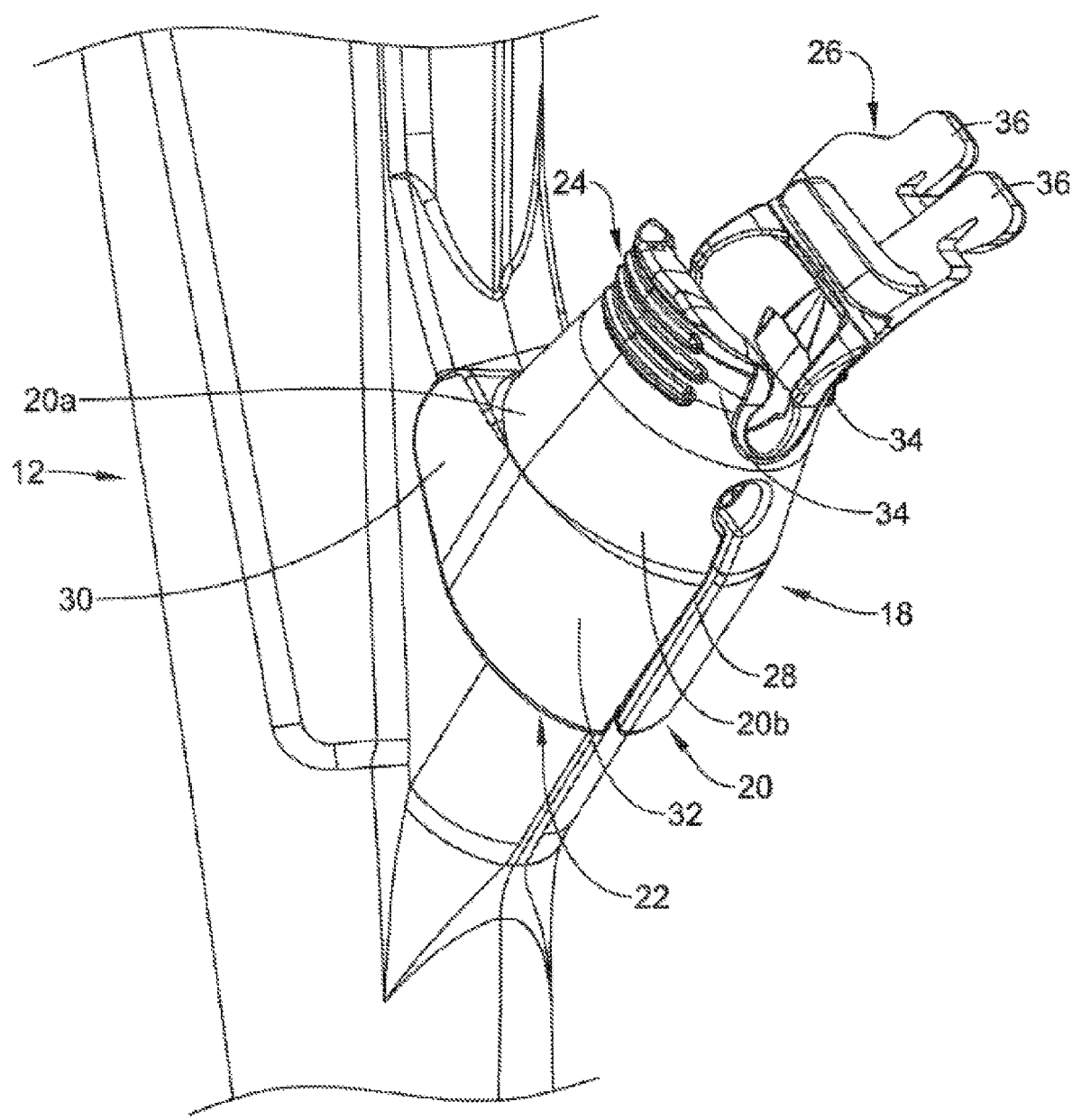
FIG. 2 is a plan view of an biopsy cap housing coupled to an endoscope, in accordance with an embodiment of the present disclosure.
Figure 3:
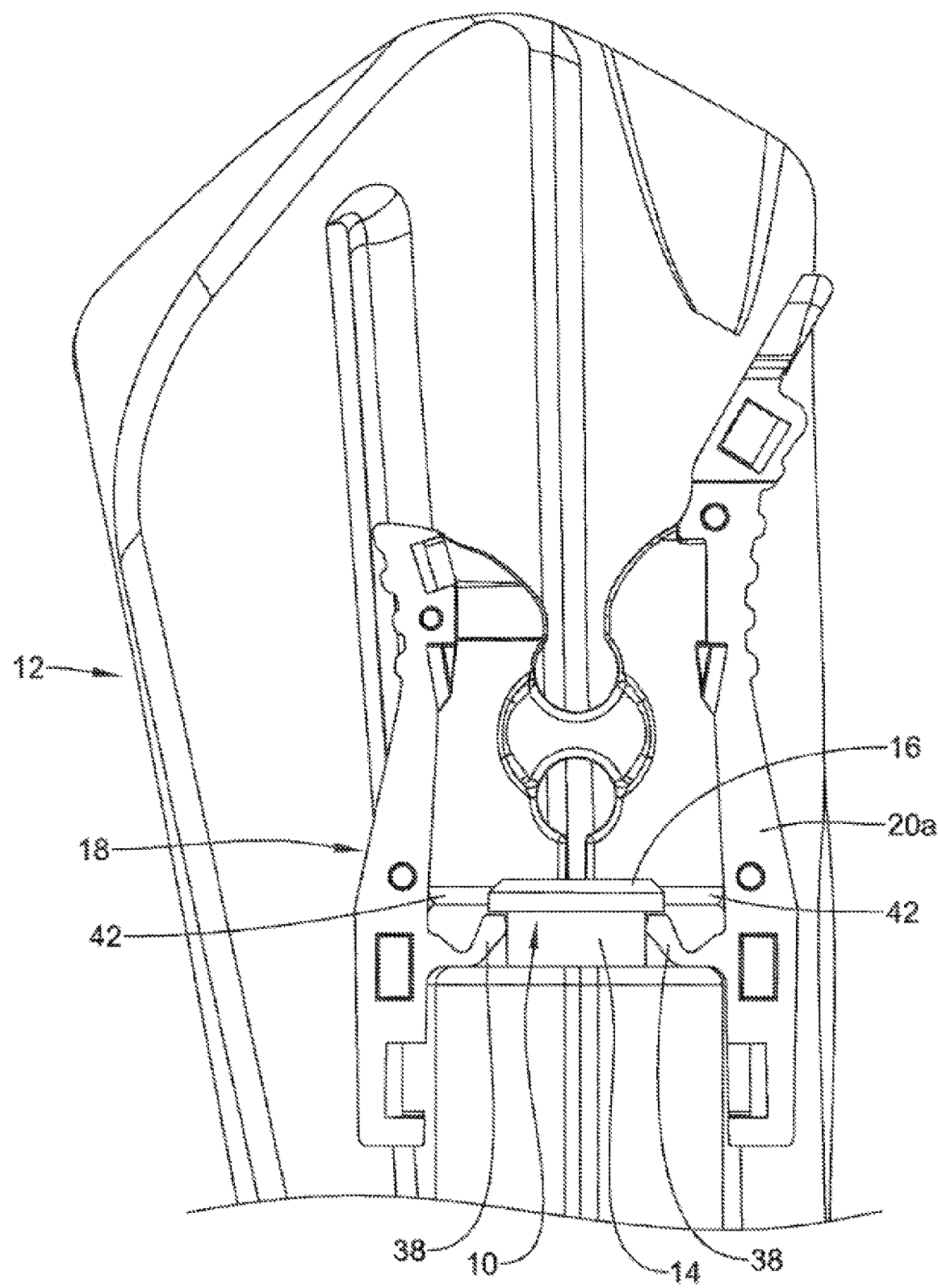
FIG. 3 is a side view of a portion of biopsy cap housing coupled to an endoscope, according to an embodiment of the present disclosure.

FIGS. 2-3 illustrates an example endoscope attachment 18 including a housing 20 coupled to the biopsy port 10. In general, the endoscope attachment 18 is designed to be coupled to (e.g., detachably coupled, attached, secured to, etc.) the biopsy port of an endoscope (e.g., the biopsy port 10 of the endoscope 12). In addition, the endoscope attachment 18 includes a number of features including the ability to form a seal with a biopsy cap at the biopsy port 10, allow for a medical instrument (e.g., a guidewire, catheter, endoscopic device, and/or the like) to pass therethrough and into the working channel of the endoscope 12, allow for the medical instrument to be secured relative to the endoscope 12, etc., and may be configured to securely receive a biopsy cap.

The endoscope attachment 18 may include a housing 20 having a skirt region 22, a grip region 24, and a locking region 26. In some instances, the housing 20 may be a single piece. In other instances, the housing 20 may be formed from 2 or more pieces, for example, first housing portion 20a and second housing portion 20b, which are secured together. In FIG. 3, for example, the second housing portion 20b is removed and only the first housing portion 20a is shown. Forming the housing 20 from separate pieces may allow for the housing 20 to be relatively easily molded (e.g., compared to a singular piece) or otherwise formed into a complex shape. When formed from separate pieces, the housing portions 20a/20b may be secured together in a suitable manner such as by pinning (e.g., snap locks that include pins on one portion and holes or openings to receive the pins on the other portion), thermal bonding, adhesive bonding, and/or the like. In various embodiments, the housing 20 may be substantially rigid. Pinning may result in secure attachment of the portions 20a, 20b and also may enhance the ability of the two portions 20a/20b of the housing to "pivot" relative to one another. When doing so, the housing 20 can open or widen (e.g., adjacent to a lower portion of the endoscope attachment 18 such as adjacent to the skirt region 22) in order to attached/detach the endoscope attachment 18 to the biopsy port 10. A slot or opening 28 may be formed along a portion of the housing 20. The slot(s) may enhance the flexibility and/or pivoting ability of the housing 20 and may make it easier to secure the endoscope attachment 18 to the biopsy port 10.

The skirt region 22 may generally be designed to follow the shape and/or contour of the endoscope 12. More particularly, the skirt region 22 may be shaped so as to conform to the shape of the handle region of the endoscope 12 adjacent to the biopsy port 10. This may increase the stability of the endoscope attachment 18 and assist with securing hold the position of the endoscope attachment 18 relative to the endoscope 12. In at least some instances, the shape of the skirt region 22 may be described as being asymmetrical. For example, the skirt region 22 may include a first portion 30 (e.g., which may or may not correspond to the first housing portion 20a) and a second portion 32 (e.g., which may or may not correspond to the second housing portion 20b).

The grip region 24 may include one or more gripping members 34. The gripping members 34 may take the form of finger or pinch grips that allow a user to grasp the endoscope attachment 18. In some instances, pinching together the gripping members 34 may widen the endoscope attachment 18 (e.g., adjacent to the skirt region 22) and allow for the endoscope attachment 18 to be more attached to/detached from the biopsy port 10. The slot 28 may help to facilitate the flexing/bending of the endoscope attachment 18 when the gripping members 34 are pinched.

The locking region 26 may include one or more locking apparatuses 36. The locking apparatuses 36 may vary in form. In some instances, the locking apparatuses 36 may take the form of hooks designed to engage and hold a medical instrument (e.g., a guidewire, catheter, endoscopic device, and/or the like). When doing so, the medical instrument can be held in place relative to the endoscope attachment 18 (and/or the endoscope 12).

Figure 4:
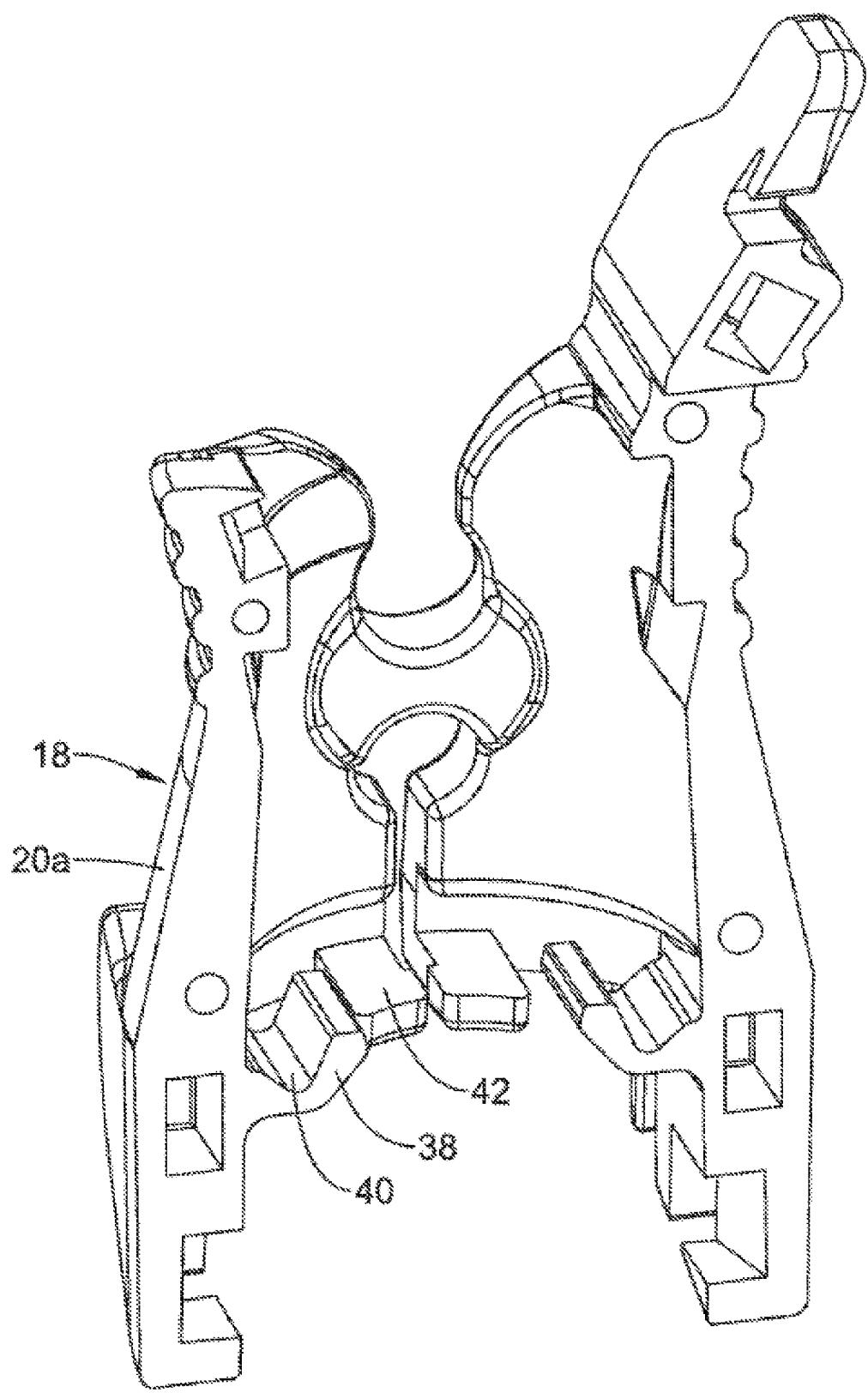
FIG. 4 is a perspective view of a biopsy cap housing, according to an embodiment of the present disclosure.

As shown in FIGS. 3 and 4, housing 20 of the endoscope attachment 18 may include one or more angled locking members 38. In general, the angled locking members 38 take the form of projections that extend radially inward and in a direction toward an upper chamber from the inner surface of the housing 20. The angled locking members 38 may include a bend, jogged, or bent region 40. In at least some instances, the angled locking members 38 may be described as being "V-shaped". However, other shapes are contemplated. The angled locking members 38 may be resiliently flexible such that the angled locking members 38 can bend or deflect in order to fit over and secure to the flanged region 16 of the biopsy port 10. The number of angled locking members 38 and/or the arrangement of the angled locking members 38 may vary. For example, the housing 20 may include two, three, four, five, six, seven, eight, or more angled locking members 38. In some instances, each center-split halves 20a, 20b includes a pair of angled locking members 38 that are arranged across from or opposite one another. When the housing portions d20a, 20b are brought together, one of the angled locking members 38 from each of the opposing housing portions 20a, 20b may be disposed adjacent to one another. Other arrangements are contemplated.

The endoscope attachment 18 may include one more stabilizing members 42. In general, the stabilizing members 42 may take the form of take the form of projections that extend radially inward from the inner surface of the housing 20. The stabilizing members 42 may help to stabilize the position (e.g., laterally and/or axially) on the biopsy port 10. The number of stabilizing members 42 and/or the arrangement of the stabilizing members 42 may vary. For example, the endoscope attachment 18 may include two, three, four, five, six, seven, eight, or more stabilizing members 42. In some instances, each housing portion 20a/20b includes a pair of stabilizing members 42 that are disposed adjacent to one another. When the housing portions 20a/20b are brought together, the pairs of stabilizing members 42 from each of the opposing housing portions 20a/20b may be disposed opposite to one another. Other arrangements are contemplated.

Figure 5:
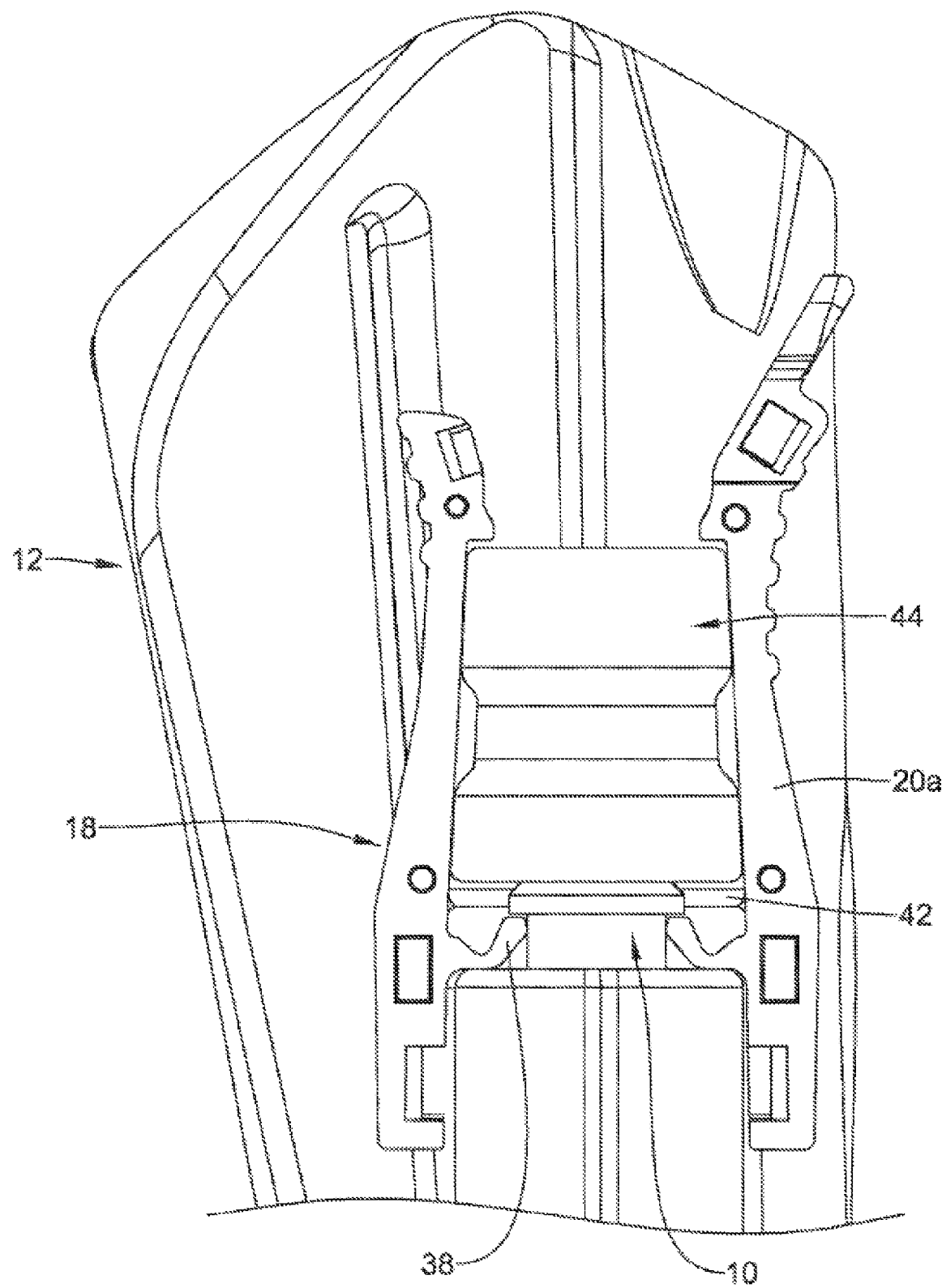
FIG. 5 is a side view of a portion of a biopsy cap housing coupled to an endoscope, according to an embodiment of the present disclosure.

A biopsy cap 44 may be disposed within the housing 20 of the endoscope attachment 18 as shown in FIG. 5. It is noted that for clarity purposes, the biopsy cap 44 is not shown in FIGS. 3-4. The biopsy cap 44 may vary in form. In at least some instances, the biopsy cap 44 may include one or more seals or sealing members (not depicted in FIG. 5).

The seal(s) may be designed to seal against the biopsy port 10 and thereby prevent fluid from leaking from the biopsy port 10. In addition, the seal(s) may be designed to seal against a medical instrument (e.g., a guidewire, catheter, endoscopic device, and/or the like) passing through the endoscope attachment 18 and/or the biopsy cap 44. In at least some instances, the biopsy cap 44 may be disposed adjacent to and/or otherwise seated on the stabilizing members 42.

Figure 6:
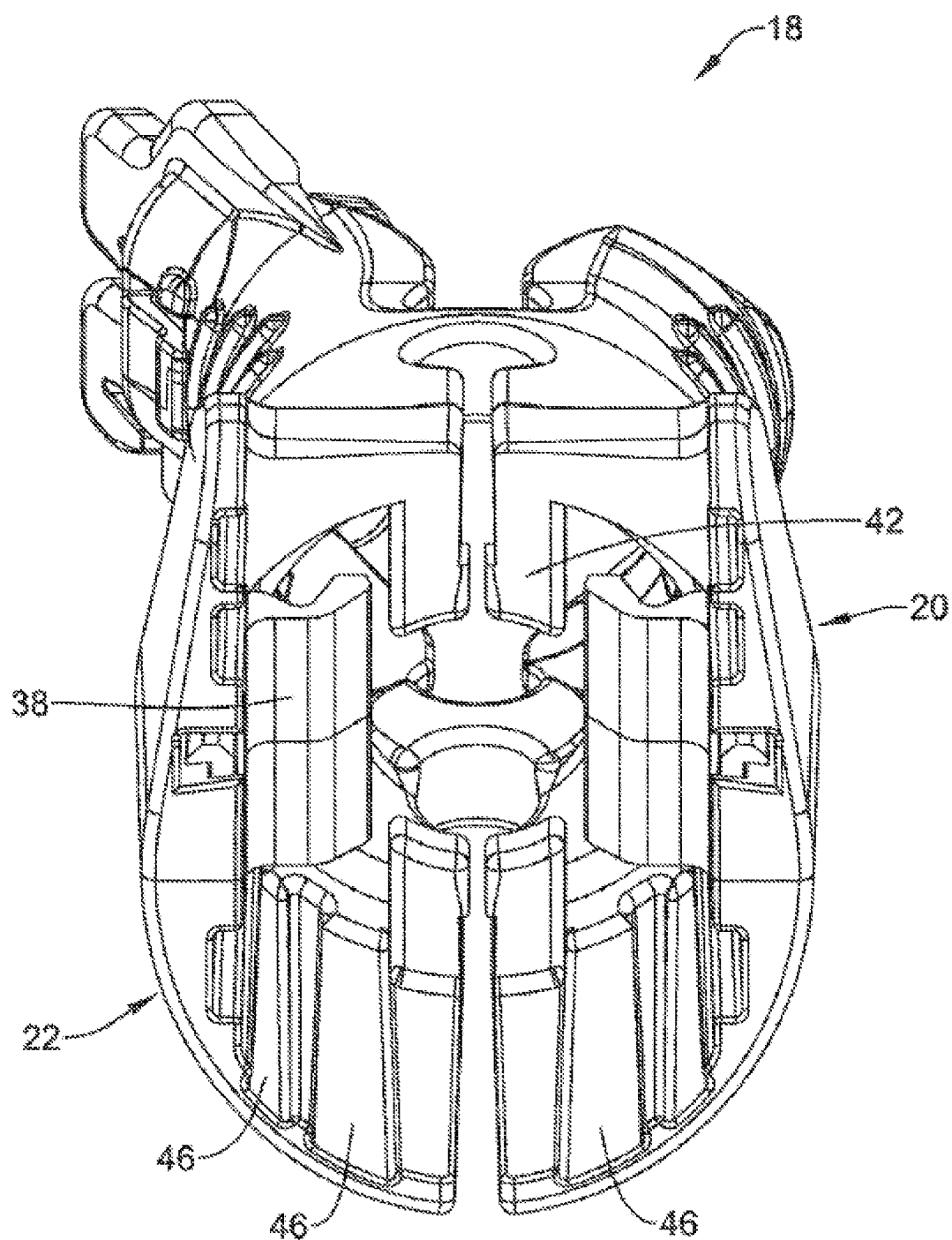
FIG. 6 is a perspective view of a biopsy cap housing, according to an embodiment of the present disclosure.

In an embodiment, a skirt region 22 may have one or more gripping members or ribs 46 disposed along an inner surface (e.g., an inner surface of the housing 20 at or along the skirt region 22) as shown in FIG. 6. The ribs 46 may help to form or otherwise define a surface along the interior of the endoscope attachment 18 that allows the endoscope attachment 18 to "grip" onto and/or otherwise frictionally engage the endoscope 12 and, thus, help to secure the endoscope attachment 18 to the endoscope 12.

Figure 7:
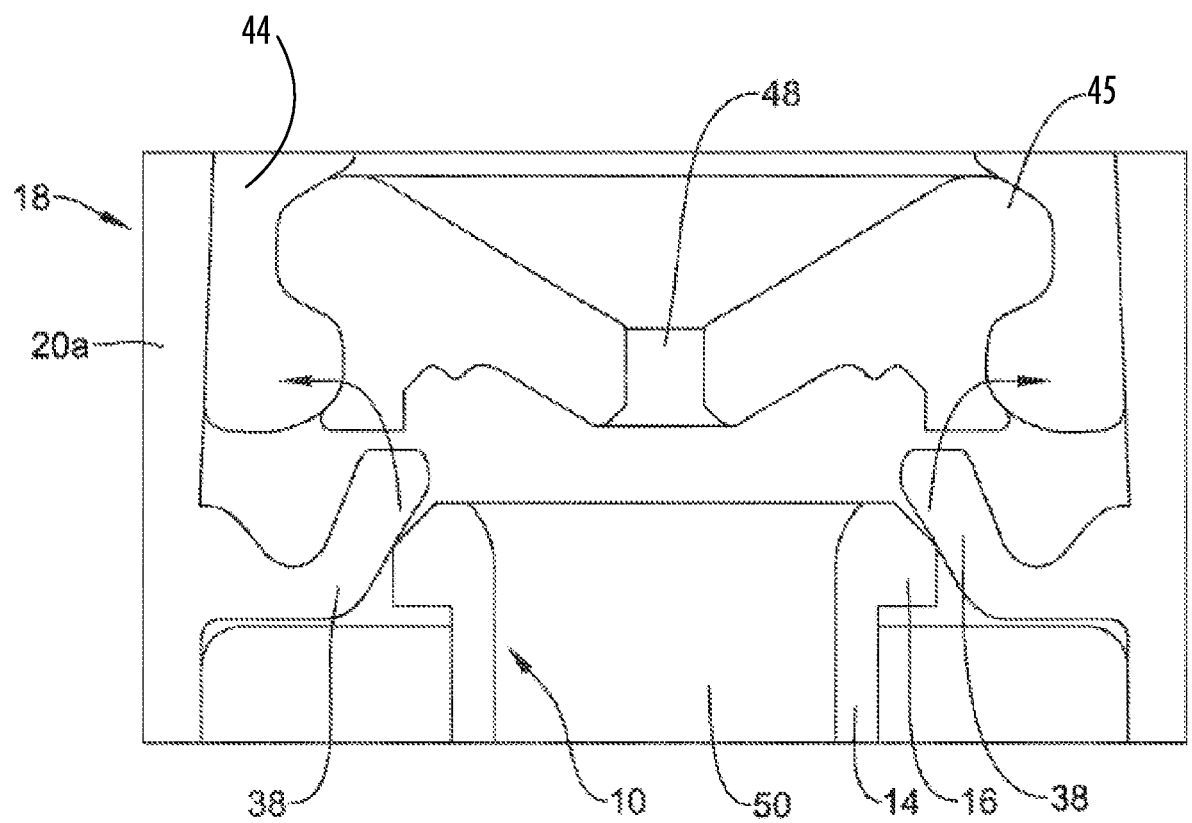
FIGS. 7 and 8 depict a biopsy cap housing being coupled to an endoscope, according to an embodiment of the present disclosure.
Figure 8:
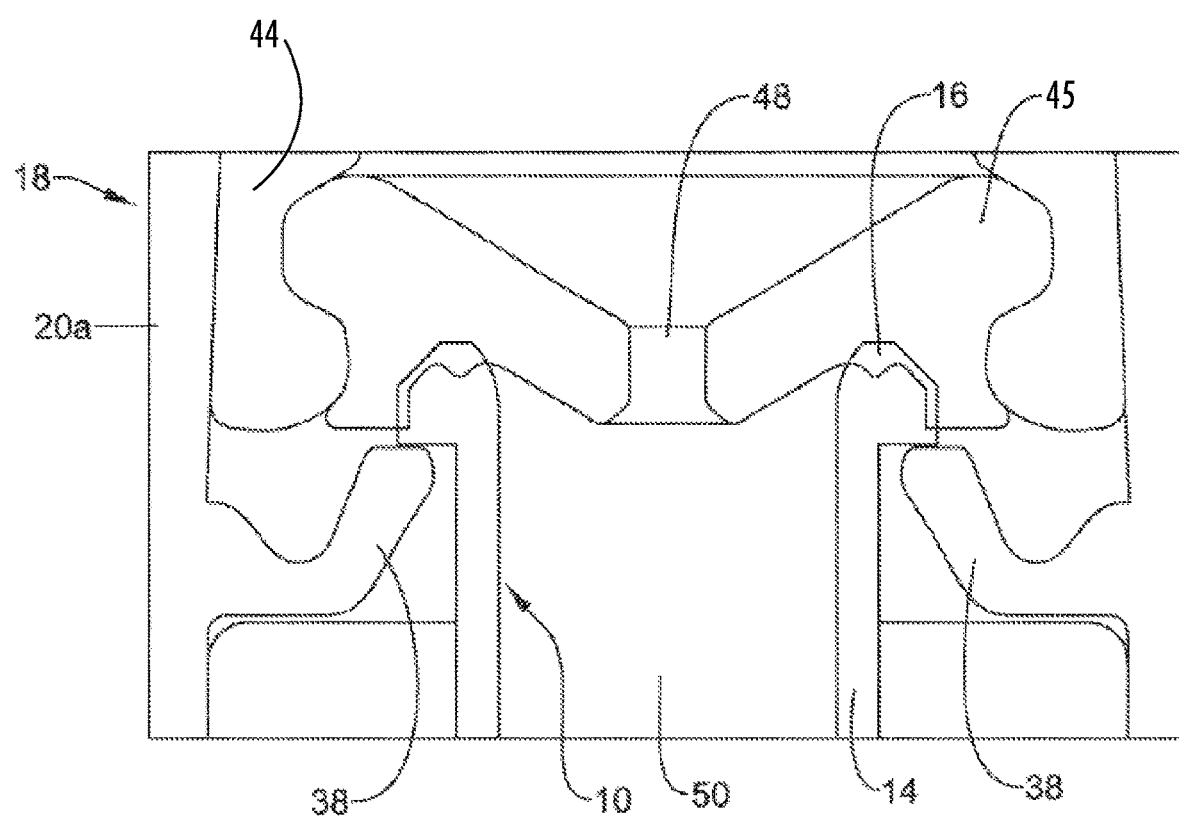

FIGS. 7 and 8 depict an embodiment of an endoscope attachment 18 with housing 20 being attached to a biopsy port 10. For example, the endoscope attachment 18 may be disposed adjacent to the biopsy port 10. When doing so, the angled locking members 38 may be brought adjacent to the flanged region 16 of the biopsy port as shown in FIG. 7. A user may apply a force (e.g., a pinching force) along a grip region (e.g., the grip region 24 of FIG. 2) of the attachment 18 to outwardly flex or otherwise pivot in order to open or widen the housing 20 (e.g., adjacent to the skirt region 22). The user may also apply a downward force onto the endoscope attachment 18 to bring the endoscope attachment into engagement with and secure the endoscope attachment 18 to the biopsy port 10. When doing so, the angled locking members 38 may resiliently deflect so that the angled locking members 38 are seated underneath the flanged region as shown in FIG. 8. When secured, the stabilizing members 42 may engage the neck region 14 and/or the flanged region 16 of the biopsy port 10. Securing the endoscope attachment 18 to the biopsy port 10 may also bring an aperture 48 of seal member 44 or a base 45 into engagement with the biopsy port 10 so that the seal member 48 may press against or otherwise seal a channel 50 of the endoscope 12 (e.g., a channel 50 accessible via the biopsy port 10). When the endoscope attachment 18 is secured to the biopsy port 10, the endoscope attachment 18 may provide haptic feedback such as a "snap" or "click" sound and/or sensation, and/or the like. A user may remove the endoscope attachment 18 by simply pinching the grip region 24 in order to flex/pivot/widen the housing 20 (as well as widen/open the angled locking members 38) and pulling the endoscope attachment 18 from the biopsy port 10.

Figure 9:
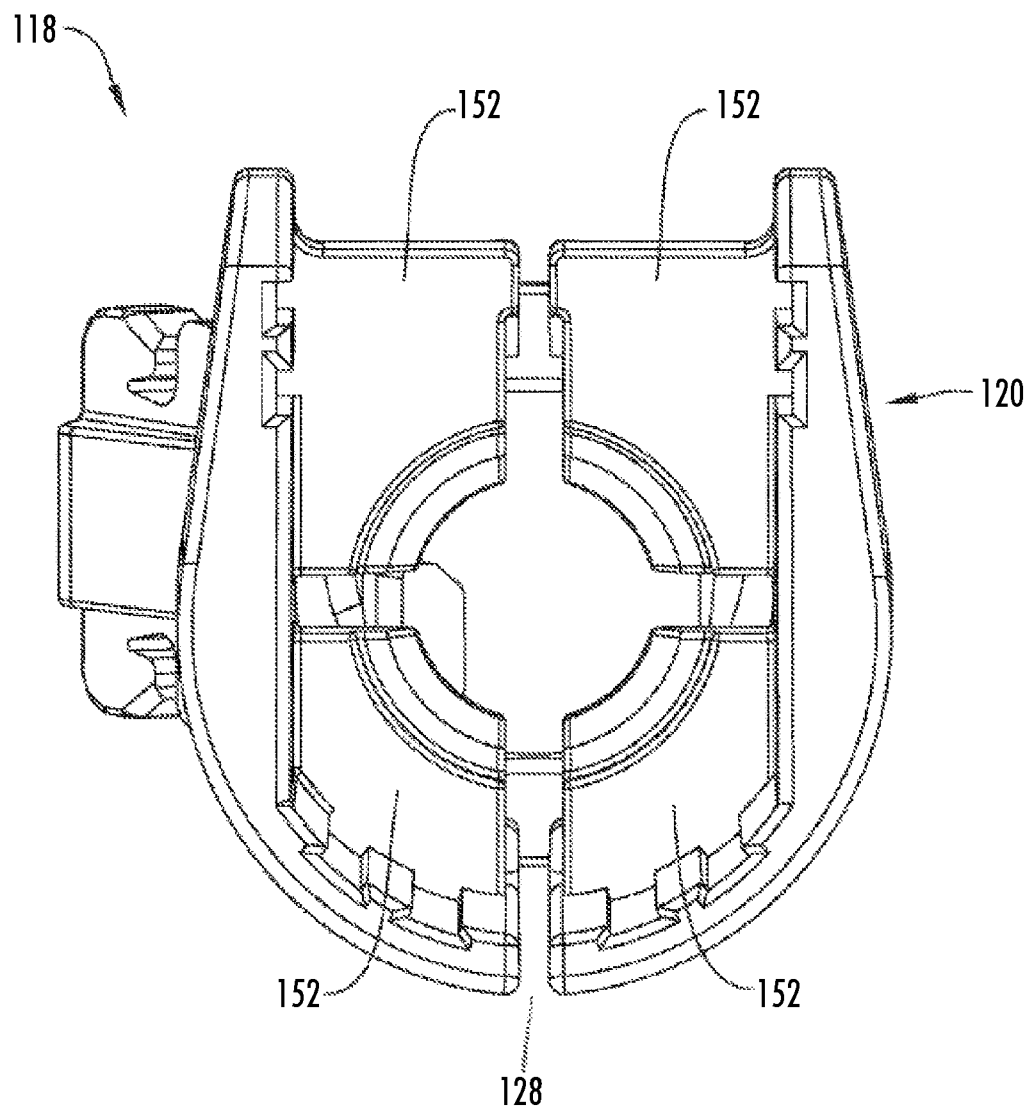
FIG. 9 is a perspective view of a biopsy cap housing, according to an embodiment of the present disclosure.

FIG. 9 illustrates an embodiment of an endoscope attachment 118 that may be similar in form and function to other endoscope attachments disclosed herein. The endoscope attachment 118 may include a housing 120. The housing 120 may be generally more flexible than the housing 20. A slot 128 may be formed in the housing to further enhance the flexibility of the housing. One or more locking members 152 may extend from the housing 120. In some instances, the locking members 152 may take the form of substantially rigid projections that extend radially inward from the housing 120. In at least some instances, the locking members 152 may be arranged to form a generally circular (e.g., and/or a broken circle) lock designed to extend around a biopsy port (e.g., such as a biopsy port 10.

Figure 10:
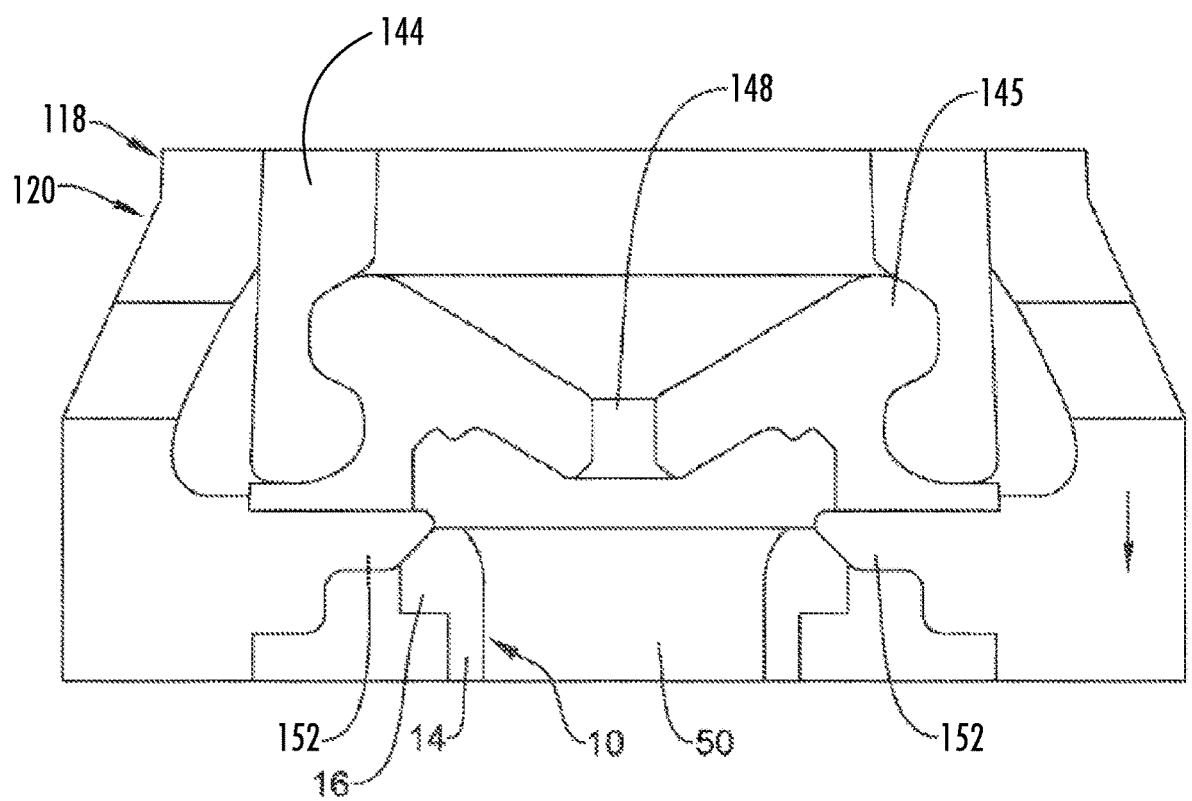
FIGS. 10 and 11 depict a biopsy cap housing being coupled to an endoscope.
Figure 11:
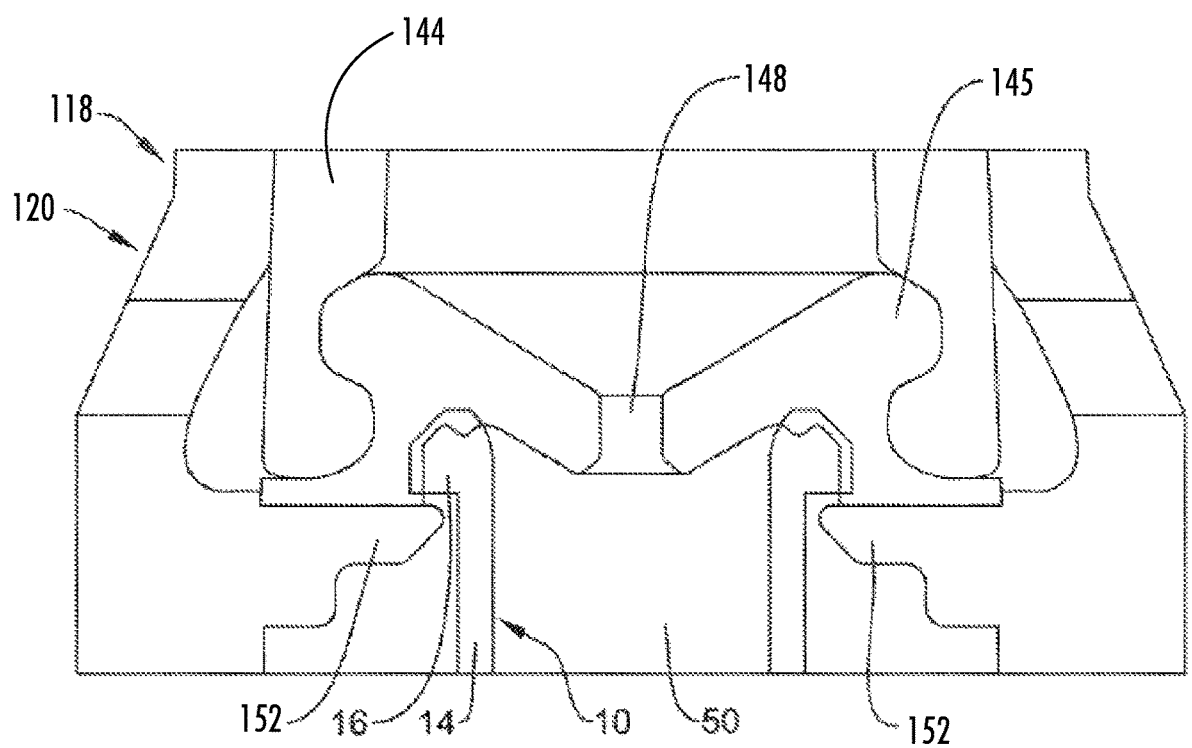

FIGS. 10 and 11 depict the endoscope attachment 118 being attached to a biopsy port 10. For example, the endoscope attachment 118 may be disposed adjacent to the biopsy port 10. When doing so, the locking members 152 may be brought adjacent to the flanged region 16 of the biopsy port as shown in FIG. 10. A user may apply a downward force onto the endoscope attachment 118 to secure the endoscope attachment 118 to the biopsy port 10. When doing so, the housing 120 may resiliently deflect so that the locking members 152 may be seated underneath the flanged region as shown in FIG. 11. Securing the endoscope attachment 118 to the biopsy port 10 may also bring an aperture 148 of the seal member 144 or a base 145 into engagement with the biopsy port 10 so that the base 145 may press against or otherwise seal a channel 50 of the endoscope 12 (e.g., a channel 50 accessible via the biopsy port 10). When the endoscope attachment 118 is secured to the biopsy port 10, the endoscope attachment 118 may provide haptic feedback such as a "snap" or "click" sound.

The materials that can be used for the various components of the endoscope attachment 18 (and/or other endoscope attachments disclosed herein) may include those commonly associated with medical instruments. For example, the endoscope attachment 18 may be made from a metal, metal alloy, polymer (some examples of which are disclosed below), a metal-polymer composite, ceramics, combinations thereof, and the like, or other suitable material. Some examples of suitable polymers may include acrylonitrile butadiene styrene, acrylonitrile butadiene styrene and polycarbonate, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-6, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An attachment for a biopsy port formed on a handle of an endoscope, the attachment comprising:
a biopsy cap having a distal end with a seal;
a housing having a chamber sized and configured to support the biopsy cap therein with the seal of the biopsy cap contacting and sealing against and across the proximal end of the biopsy port;
one or more locking members extending radially-inwardly from an inner surface of the housing, the locking members being positioned to engage the biopsy port; and
one or more stabilizing members extending radially-inwardly from the inner surface of the housing and circumferentially spaced apart from the one or more locking members, and positioned to engage the biopsy port and to stabilize a lateral position of the attachment with respect to the biopsy port.

2. The attachment of claim 1, wherein the one or more locking members include a first locking member disposed on a first side of the inner surface of the housing and a second locking member disposed on a second side of the inner surface of the housing.

3. The attachment of claim 1, wherein the one or more locking members include a first angled locking member, and wherein the first angled locking member includes a bent region.

4. The attachment of claim 1, wherein the one or more locking members include a first angled locking member, and wherein the first angled locking member is substantially V-shaped.

5. The attachment of claim 1, wherein the one or more locking members include a first angled locking member and wherein the first angled locking member is substantially rigid.

6. The attachment of claim 1, wherein the one or more locking members include a first angled locking member and wherein the first angled locking member is resiliently deflectable.

7. The attachment of claim 1, wherein the one or more stabilizing members include a first stabilizing member disposed on a first side of the inner surface of the housing and a second stabilizing member disposed on a second side of the inner surface of the housing.

8. The attachment of claim 1, wherein the one or more stabilizing members are positioned below the chamber for the biopsy cap to support the biopsy cap within the chamber of the housing.

9. The attachment of claim 1, wherein the housing includes a skirt region.

10. The attachment of claim 1, wherein:
the locking members are positioned to engage a neck region of the biopsy port formed on the handle of the endoscope; and
the stabilizing members are positioned to engage the neck region and/or the radially-outward periphery of a flanged region proximal to the neck region of the biopsy port formed on the handle of the endoscope.

11. The attachment of claim 1, wherein the biopsy cap is seated on the stabilizing member.

12. An attachment for a biopsy port formed on a handle of an endoscope having a surface surrounding the biopsy port, the attachment comprising:
a housing designed to engage the endoscope and having a first end region and a second end region;
a skirt region defined around the first end region of the housing and defining a skirt shape prior to engagement with an endoscope corresponding to the shape of the surface surrounding the biopsy port to engage the surface surrounding the biopsy port to stabilize the housing relative to the endoscope;
a locking member extending radially-inwardly from an inner surface of the housing between the first end region and the second end region of the housing to engage the biopsy port; and
a stabilizing member extending radially-inwardly from the inner surface of the housing between the first end region and the second end region of the housing and disposed adjacent to and circumferentially spaced apart from the locking member and to engage the handle of the endoscope.

13. The attachment of claim 12, wherein:
the locking member is positioned to engage a neck region of the biopsy port formed on the handle of the endoscope; and
the stabilizing member is positioned to engage the neck region and/or the radially-outward periphery of a flanged region proximal to the neck region of the biopsy port formed on the handle of the endoscope.

14. The attachment of claim 12, wherein the locking member includes a bent region.

15. The attachment of claim 12, wherein the locking member is substantially V-shaped.

16. The attachment of claim 12, wherein the locking member is substantially rigid.

17. The attachment of claim 12, wherein the locking member is resiliently deflectable.

18. The attachment of claim 12, further comprising a second stabilizing member extending from the inner surface of the housing and disposed opposite the stabilizing member.

19. The attachment of claim 12, wherein the stabilizing member is positioned to support a biopsy cap within the housing.

20. An attachment for a biopsy port of an endoscope, the attachment comprising:
a housing designed to engage the biopsy port of the endoscope and to receive a biopsy cap in a proximal end region of the housing;
a skirt region defined circumferentially along a distal end region of the housing and having a set asymmetrical shape defined prior to engagement with the endoscope to correspond with the shape of the endoscope, and configured to engage the endoscope to stabilize the housing relative to the endoscope;
a pair of circumferentially spaced apart locking members extending radially-inwardly from an inner surface of the housing in a direction towards one another to engage a neck region of the biopsy port; and
a pair of circumferentially spaced apart stabilizing members extending radially-inwardly from the inner surface of the housing in a direction towards one another to engage the radially-outward periphery of a flanged region proximal to the neck region of the biopsy port, and disposed adjacent to and circumferentially spaced apart from the pair of circumferentially spaced apart locking members.

* * * * *